US012731658B2

(12) United States Patent
Ivanov et al.

(10) Patent No.: US 12,731,658 B2
(45) Date of Patent: Sep. 8, 2026

(54) METHODS FOR DETECTING COPY-NUMBER VARIATIONS IN NEXT-GENERATION SEQUENCING

(71) Applicant: SOPHIA GENETICS S.A., Saint Sulpice (CH)

(72) Inventors: Dmitri Ivanov, Pully (CH); Zhenyu Xu, Nyon (CH)

(73) Assignee: Sophia Genetics, S.A., Rolle (CH)

( * ) Notice: Subject to any disclaimer, the term of this patent is extended or adjusted under 35 U.S.C. 154(b) by 970 days.

(21) Appl. No.: 15/777,091

(22) PCT Filed: Nov. 18, 2016

(86) PCT No.: PCT/EP2016/078113
§ 371 (c)(1),
(2) Date: May 17, 2018

(87) PCT Pub. No.: WO2017/085243
PCT Pub. Date: May 26, 2017

(65) Prior Publication Data
US 2018/0330046 A1 Nov. 15, 2018

Related U.S. Application Data

(60) Provisional application No. 62/256,748, filed on Nov. 18, 2015.

(51) Int. Cl.
*G16B 20/10* (2019.01)
*G16B 20/00* (2019.01)
(Continued)

(52) U.S. Cl.
CPC ............. *G16B 20/10* (2019.02); *G16B 20/00* (2019.02); *G16B 30/00* (2019.02); *G16B 30/10* (2019.02); *G16B 20/20* (2019.02)

(58) Field of Classification Search
CPC ........ G16B 20/00; G16B 20/10; G16B 20/20; G16B 30/00; G16B 30/10; G16B 40/00; G16B 25/00; G16B 40/20; G16B 25/10; G16B 40/30; G16B 5/20; G16B 50/00; G16B 35/20; G16B 25/20; G16B 45/00; C12Q 2600/156; C12Q 1/6883; C12Q 2537/16; C12Q 2537/165; C12Q 1/6858; C12Q 1/686; C12Q 1/6827; C12Q 2600/112; C12Q 2535/122; C12Q 1/6809; C12Q 2537/159; C12Q 2545/101; C12Q 1/6869; G16H 10/40; G16H 50/30; G16H 50/50; G16Z 99/00; C12N 15/1093; G06F 17/18; G06F 18/00; G06F 18/2115; G06F 18/22; G06F 18/295; G06F 18/29; G06F 18/2113; G06N 20/00; G06N 3/08; G06N 7/005; G06N 7/01; G06N 7/00; G06N 3/0895
See application file for complete search history.

(56) References Cited

U.S. PATENT DOCUMENTS

2014/0296094 A1 10/2014 Domanus
2016/0017412 A1* 1/2016 Srinivasan ........... C12Q 1/6869 506/2

(Continued)

FOREIGN PATENT DOCUMENTS

CN 104221022 A 12/2014
CN 104830993 A 8/2015

(Continued)

OTHER PUBLICATIONS

Backenroth, d. et al. (2014) CANOES: detecting rare copy number variants from whole exome sequencing data. Nucleic Acids Research 42:12 e97, 9 pages. (Year: 2014).*
Amarasinghe et al. CoNVEX: copy number variation estimation in exome sequencing data using HMM. BMC bioinformatics 2013 14 (suppl 2) S2, 9 pages. (Year: 2013).*
Jiang et al. CODEX: a normalization and copy number variation detection method for whole exome sequencing. Nucleic Acid Research (2015) 43:6 e39 12 pages. (Year: 2015).*
Plagnol, V. (2012) A robust model for read count data in exome sequencing experiments and implications for copy number variant calling. Bioinformatics vol. 28, No. 21, p. 2747-2754 (and supplemental information). (Year: 2012).*

(Continued)

*Primary Examiner* — Mary K Zeman
(74) *Attorney, Agent, or Firm* — Bochner PLLC; Andrew Bochner; Caitlin Hyland

(57) ABSTRACT

Copy Number Variants (CNV) detection methods described herein may efficiently integrate CNV detection into the workflow for a next generation sequencer (NGS) data processing, in parallel with SNP and INDEL variant calling. CNV detection methods as described herein may be performed by analyzing the coverage pattern across a suitable set of genomic regions or amplicons and across a batch of samples from different patients. The proposed methods do not require the use of specifically chosen reference samples as inputs to the workflow, but rather automatically select a set of reference samples from the same batch, for each sample being tested. The CNV detection methods may reliably detect CNVs in a set of samples without prior assumptions about the CNV status of any of those samples. Embodiments described herein may also apply the CNV detection scheme iteratively to further improve the detection performance, especially in the case of more frequent CNV occurrence. Since the knowledge on the CNVs in reference samples may improve their comparison with the sample being tested, the proposed methods may further comprise the step of iteratively feeding back the information about the CNVs found in the samples from any detection step into the next iteration step. The proposed methods may also further use additional information available from the NGS workflow about the samples, such as information on SNP fractions, as input to the NGS CNV detection.

12 Claims, 4 Drawing Sheets

(51) Int. Cl.

| | |
|---|---|
| ***G16B 20/20*** | (2019.01) |
| ***G16B 30/00*** | (2019.01) |
| ***G16B 30/10*** | (2019.01) |

(56) References Cited

U.S. PATENT DOCUMENTS

| | | | | |
|---|---|---|---|---|
| 2016/0275240 A1* | 9/2016 | Huelga | ................ | C12Q 1/6806 |
| 2016/0300013 A1* | 10/2016 | Ashutosh | ............... | G16B 20/20 |
| 2016/0340722 A1 | 11/2016 | Platt | | |
| 2018/0330046 A1* | 11/2018 | Ivanov | ................... | G16B 20/00 |
| 2022/0101944 A1 | 3/2022 | Ivanov et al. | | |
| 2022/0130488 A1 | 4/2022 | Ivanov et al. | | |

FOREIGN PATENT DOCUMENTS

| | | |
|---|---|---|
| WO | 2014/083147 | 6/2014 |
| WO | 2014/151511 | 9/2014 |
| WO | 2015/112619 | 7/2016 |

OTHER PUBLICATIONS

Wang, Weibo et al. (Apr. 16, 2015) Allele-specific copy-number discovery from whole-genome and whole-exome sequencing. Nucleic Acids Research, vol. 43, No. 14, e90, 18 pages, plus some supplemental information. (Year: 2015).*

Eddy (2004) "What is a hidden Markov model?" Nature Biotechnology, vol. 22, No. 10 p. 1315-1316. (Year: 2004).*

Kadalayil et al (Aug. 2014) Exome sequence read depth methods for identifying copy number changes. Briefings in Bioinformatics, vol. 16, No. 3, p. 380-392 (Year: 2014).*

Illumina (2015) Sequencing power for every scale. 16 pages. (Year: 2015).*

Illumina (2015) MiSeq® system specification sheet. 4 pages. (Year: 2015).*

Illumina (2015) Nextera® Rapid Capture Enrichment Protocol Guide. 18 pages. (Year: 2015).*

Illumina (2016) Nextera® Rapid Capture Enrichment Reference Guide, 60 pages. (Year: 2016).*

Illumina (2012-2014) Nextera® Rapid Capture Exomes data sheet, 4 pages. (Year: 2014).*

PCT Search Report and IPER in PCT/EP2016/078113.

Agilent Technologies (2012) SureSelect RNA Target Enrichment for Illumina Paired-End Sequencing Protocol, version 2.2.1, Feb. 2012. 76 pages. (Year: 2012).

Chen, C. et al. (2014) Software for pre-processing Illumina next-generation short read sequences. Source Code for Biology and Medicine, vol. 9:8, 11 pages. (Year: 2014).

Final Office Action of the United States Patent and Trademark Office in related U.S. Appl. No. 17/505,934, dated Oct. 8, 2025, 40 pages.

Final Office Action of the United States Patent and Trademark Office in related U.S. Appl. No. 17/505,943, dated Oct. 14, 2025, 26 pages.

Fromer, M. (Apr. 24, 2014) Using XHMM software to detect copy number variation in whole exome sequencing data. Current Protocols in Human Genetics, vol. 81: 7.23.1-7.23.21. (Year: 2014).

Illumina (2016) Nextera® Rapid Capture Enrichment Reference Guide, 60 pages. Revision history illustrates capabilities added between 2013 and 2016. The disclosure includes quantifying enriched targets in the Appendix. (Year: 2016).

Marioni J. C, et al. (2007) Breaking the waves: improved detection of copy number variation from microarray based comparative genomic hybridization. Genome Biology, vol. 8: R228. (Year: 2007).

TAO Dan, "Study on the Genetic Variation Profile of Lung Squamous Cell Carcinoma in the Chinese Population", China Doctoral Dissertations Full-text Database (CDFD), Medical and Health Sciences Collection, vol. 2015, Issue No. 11, Nov. 15, 2015, 193 pages.

Third Office Action of the China Patent Office in related Chinese Appl. No. 201680067423.2 , dated Apr. 30, 2026, 12 pages.

* cited by examiner

METHODS FOR DETECTING COPY-NUMBER VARIATIONS IN NEXT-GENERATION SEQUENCING

FIELD OF THE INVENTION

Methods described herein relate to genomic analysis in general, and more specifically to next generation sequencing applications.

BACKGROUND OF THE INVENTION

Next-Generation Sequencing

Next-generation sequencing (NGS) or massively parallel sequencing (MPS) technologies have significantly decreased the cost of DNA sequencing in the past decade. NGS has broad application in biology and dramatically changed the way of research or diagnosis methodologies. For example, RNA expression profiling or DNA sequencing can only be conducted with a few numbers of genes with traditional methods, such as quantitative PCR or Sanger sequencing. Even with microarrays, profiling the gene expression or identifying the mutation at the whole genome level can only be implemented for organisms whose genome size is relatively small. With NGS technology, RNA profiling or whole genome sequencing has become a routine practice now in biological research. On the other hand, due to the high throughput of NGS, multiplexed methods have been developed not just to sequence more regions but also to sequence more samples. Compared to the traditional Sanger sequencing technology, NGS enables the detection of mutation for much more samples in different genes in parallel. Due to its superiorities over traditional sequencing method, NGS sequencers are now replacing Sanger in routine diagnosis. In particular, genomic variations of individuals can now be routinely analyzed for a number of medical applications ranging from genetic disease diagnostic to pharmacogenomics fine-tuning of medication in precision medicine practice. NGS consists in processing multiple fragmented DNA sequence reads, typically short ones (less than 300 nucleotide base pairs). The resulting reads can then be compared to a reference genome by means of a number of bioinformatics methods, to identify small variants such as Single Nucleotide Polymorphisms (SNP) corresponding to a single nucleotide substitution, as well as short insertions and deletions (INDEL) of nucleotides in the DNA sequence compared to its reference.

Targeted Enrichment

In some pathologies, a specific gene variant has been associated with the illness, such as the BRCA1 and BRCA2 genes in certain forms of hereditary breast and ovarian cancers or the CFTR gene in cystic fibrosis. Rather than sequencing the whole genome (WGS) from an individual sample, the genomic analysis can focus on the genome region associated with the illness, by targeting, with a set of region-specific DNA primers or probes, and enriching or amplifying, for instance with PCR (Polymerase Chain Reaction), the biological DNA sample specifically for sub-regions corresponding to the gene along the DNA strand. A number of next generation sequencing assays have now been developed along those principles as ready-to-use biological kits, such as for instance the Multiplicom MASTR or the Illumina TruSeq® Amplicon assay kits to facilitate DNA based diagnostics with next generation sequencers, such as for instance the Illumina MiSeq® sequencer, in medical research and clinical practice.

Target enrichment may be achieved from a small sample of DNA by means of probe-based hybridization (on arrays or in-solution) or highly multiplexed PCR-based targeted exon enrichment, so that both the gene coverage/read depth and the amplification specificity (amplifying the right region, as measured by further alignment to the desired target regions) are maximized. Examples of commercially available target enrichment systems include Agilent SureSelect™ Target Enrichment System, Roche NimbleGen SeqCap EZ, Illumina Nextera Rapid Capture, Agilent Haloplex™ and Multiplicom MASTR™.

In order to maximize the use of the massively-parallel processing NGS sequencer, a number of samples are multiplexed in the targeted NGS experiment—a pool of 48 or more target enrichment samples can thus be simultaneously input to the Illumina MiSeq sequencer for instance. Raw sequencing data out of the NGS sequencer may then be analyzed to identify specific subsequences, for instance by alignment to a reference genome. As a result, the amplification may produce more than a thousand reads for a given amplicon in a patient sample.

CNV Detection

In practice, beyond SNPs and INDELs, a number of pathologic genetic variants are caused by more significant changes in the DNA sequence. A copy-number variant ("Copy-number value", "Copy-number variation", or CNV) quantifies the number of copies of a particular region in the sample DNA sequence, that may be subject to long duplications (number of copies above the normal value) or deletions (number of copies below the normal value) of possibly more than several hundreds of nucleotides when compared to the reference genome. While next generation sequencing methods have been shown more efficient than traditional Sanger sequencing in the detection of SNPs and INDELs, detection of CNVs in targeted NGS raises a number of specific challenges for alignment to the reference genome or matching to some specific subsequences, as the read length is typically lower than 300 bp, i.e. a shorter sequence than the overall CNV regions. State-of-the-art CNV detection methods such as MLPA (Multiplex Ligation-dependent Probe Amplification) still require a separate experiment and genomic analysis workflow. This limits the advantages of NGS in practical genomic analysis applications, as different workflows to process different patient samples need to be conducted to detect the CNVs of pathological importance. Also, the state of the art CNV detection methods are low throughput and cannot simultaneously check CNVs for a large number of samples and regions in parallel. A number of solutions have thus been recently proposed in the literature to better address CNV detection with NGS workflows. One approach, as described for instance in WO2014151511, consists in comparing the level of target amplicons to the level of a control amplicon so as to determine the presence of a CNV. However, this method is very sensitive to the choice of the control amplicon, which may not be readily available. Another approach consists in further optimizing the target enrichment step so as to have a better reference for CNV detection from the target enrichment sample pool itself. For instance, WO2015112619 discloses the use of dummy primers to assign a unique set of reference nucleotide sequences to each bin of pre-sorted amplicons, at the expense of an extra PCR amplification step and iterative exhaustive search by the CNV detection module. WO2014083147 proposes to optimize the PCR primers with a complementary region to the sequence to be analyzed on the 3' end and a non-complementary region on the 5' end. The latter methods require the use of a specific assay kit, which is too limitative for many current applications.

There is therefore a need for a better solution to efficiently detect CNVs, possibly for a large number of samples and regions simultaneously, within a single targeted Next Generation Sequencing experiment, regardless of which underlying target enrichment technology has been used, and in as automated a workflow as possible to facilitate the research and clinical laboratory practice over the prior art methods.

BRIEF SUMMARY

The foregoing advantages may be achieved by a method for detecting copy number values (CNV) from a pool of DNA samples enriched with a target enrichment technology, each enriched DNA sample being associated with a library of pooled fragments from a set of amplicons/regions, each amplicon/region being sequenced with a high-throughput sequencer to generate coverage count for each sample and for each amplicon/region, comprising: normalizing, with a data processing unit, the coverage count associated with each sample; selecting, with a data processing unit, for each sample, a set of reference samples, within the pool of DNA samples, as the samples with the closest normalized coverage count to said sample normalized coverage count; and for each sample, estimating the copy number values in said sample as a function of at least the coverage counts in said sample and of at least the coverage counts in the selected set of reference samples for said sample.

The number of reference samples may be a function of the total number of samples. It may be smaller than the total number of samples.

Selecting a set of reference samples may comprise calculating a distance between the coverage counts normalized both within each sample/plex and within each region. The distance may be the Euclidean distance.

Normalizing the coverage count and/or selecting a set of reference samples may depend on an estimate of the copy number values for each sample and for each amplicon/region at a previous iteration. The prior estimate of the copy number values may be pre-defined. The prior estimate of the copy number values may be calculated iteratively, starting with a pre-defined prior estimate of the copy number values and using the result of the CNV detection at each iteration as the prior estimate of the copy number values in the subsequent iteration, until the copy number values estimate converges, reaches a cycle, or the number of iterations reaches a pre-defined limit.

For each sample and for each amplicon/region, the likelihood for each possible copy number value may be estimated. A Hidden Markov Model may be further used to estimate the copy number values and their confidence levels for each amplicon/region. Possible copy number values for which the confidence level is below a minimum threshold may be filtered out from the results.

The estimate of the copy number values may be calculated using information on the SNP fractions and coverage count.

A principal-component filter may be applied to the coverage count.

The number of reference samples may depend on the iteration index. In one iteration, the number of reference samples $N_R$ may equal the total number of samples N, while at another iteration the number of reference samples $N_R$ may be different from the total number of samples N.

DETAILED DESCRIPTION

Genomic Analysis System

Figure 1:
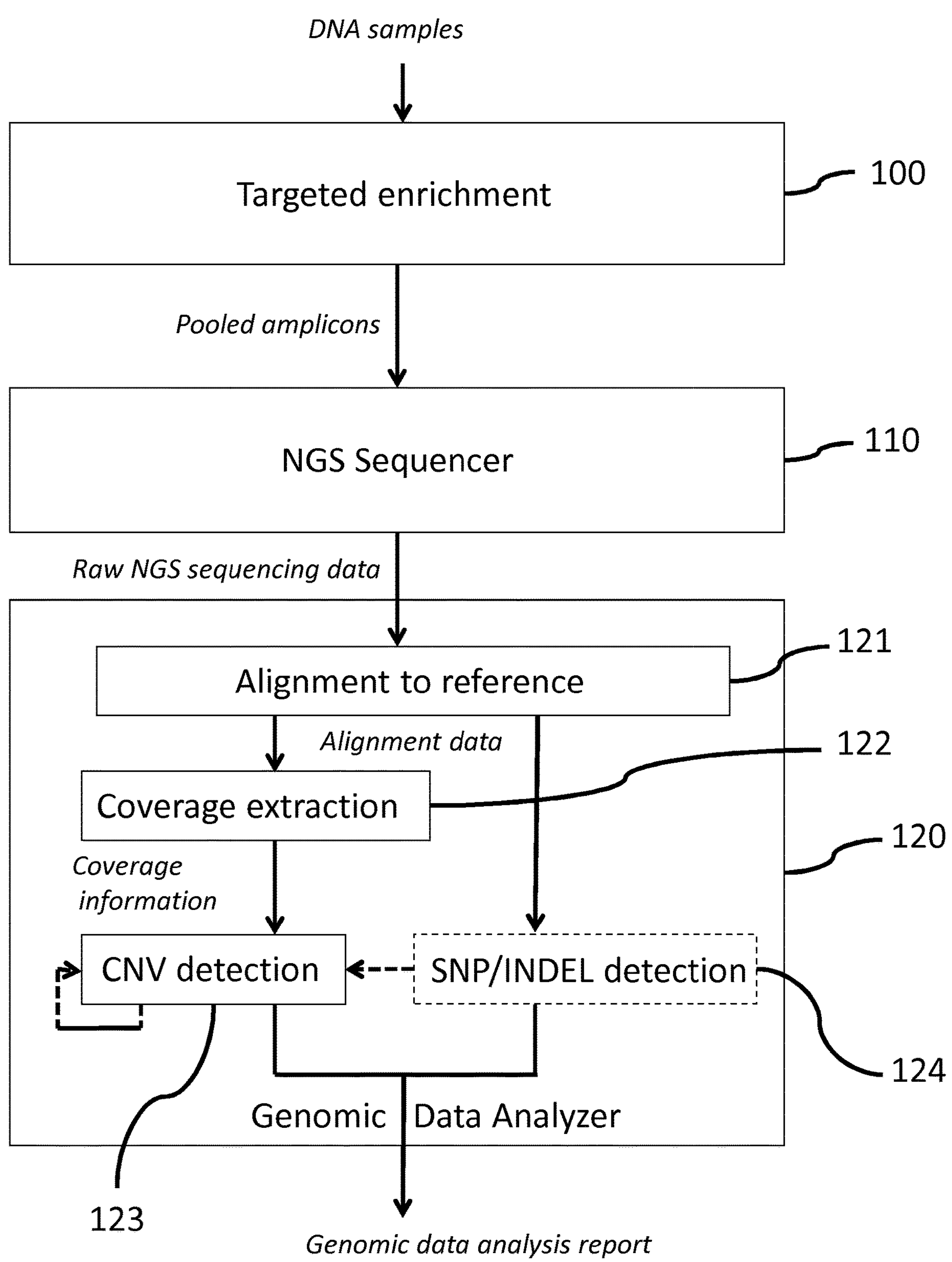
FIG. 1 represents a targeted NGS genomic analysis functional workflow.

FIG. 1 shows an exemplary genomic analysis system in accordance with a possible embodiment of the disclosure, comprising a targeted enrichment assay 100, a next generation sequencer 110 and a genomic data analyzer 120.

A pool of DNA samples is processed by the targeted enrichment assay 100 to generate a library of DNA fragments prepared by amplicon-based enrichment or probe-based enrichment as input to the next generation sequencer 110, each set of fragments corresponding to a different DNA sample. The number of fragments is application dependent. For example, in some amplicon-based experiments, target enrichment may require 150 primers to enrich 75 different regions to be targeted out of the sample genome. In other probe-based experiments, probe enrichment may select, for example, DNA fragments from 413 selected regions. The number of samples may also be adapted to the next-generation sequencing sequencer 110 parallel processing capability, for instance 48 samples may be sequenced in parallel by an Illumina MiSeq sequencer. Other NGS sequencer technologies may be used, such as for instance the Roche 454™ GS Junior or GS FLX, Illumina MiSeq®, or Life Technologies Ion PGM™ sequencers.

The next-generation sequencer 110 analyses the input samples and generates sequence reads in a computer-readable file format representing raw NGS sequencing data. Depending on the NGS technology, one or more files may be output by the NGS sequencer 110. In some embodiments, the FASTQ file format may be used with two different files for forward and reverse reads or as a single joined file. Other embodiments are also possible. The raw NGS sequencing data is further input to the genomic data analyzer 120.

The genomic data analyzer 120 computer system (also “system” herein) 120 is programmed or otherwise configured to implement different genomic data analysis methods, such as receiving and/or combining sequencing data and/or annotating sequencing data.

The genomic data analyzer 120 may be a computer system or part of a computer system including a central processing unit (CPU, “processor” or “computer processor” herein), memory such as RAM and storage units such as a hard disk, and communication interfaces to communicate with other computer systems through a communication network, for instance the internet or a local network. In some embodiments, the computer system may comprise one or more computer servers, which may enable distributed computing, such as cloud computing, for instance in a genomic data farm. In some embodiments, the genomic data analyzer 120 may be integrated into a massively parallel system. In some embodiments, the genomic data analyzer 120 may be directly integrated into a next generation sequencing system.

As illustrated on FIG. 1, the genomic data analyzer 120 may comprise an alignment module 121, which compares the raw NGS sequencing data to a reference genome. The alignment results (which may be represented as one or several files in BAM, SAM or other similar formats, as known to those skilled in the bioinformatics art) may be further analyzed in search for SNP and INDEL polymorphisms by means of a SNP/INDEL detection module 124. Alignment information may be further filtered and analyzed to retrieve coverage information (or coverage count). In an embodiment of the present disclosure, a coverage extraction module 122 may process the alignment data to extract coverage information in accordance with the targeted enrichment 100 and NGS sequencer 110 technologies applied upstream in the overall genomic analysis workflow. A CNV detection module 123 in accordance with the disclosure may then analyze the coverage information to identify and qualify copy-number variants (CNVs) in the original DNA samples. In some embodiments, the CNV detection module 123 may operate iteratively, by using CNV detection information from a former step in a next iteration. As can be seen in FIG. 1, the same NGS experiment with a single target enrichment step 100 and a single sequencing step 110 can thus be used to analyze different SNP/INDELs and CNV genomic variants simultaneously, instead of running separate NGS/SNP-INDELS detection and MLPA/CNV detection experiments as in the prior art genomic data analysis workflows.

CNV Detection—Overall Scheme

Figure 2:
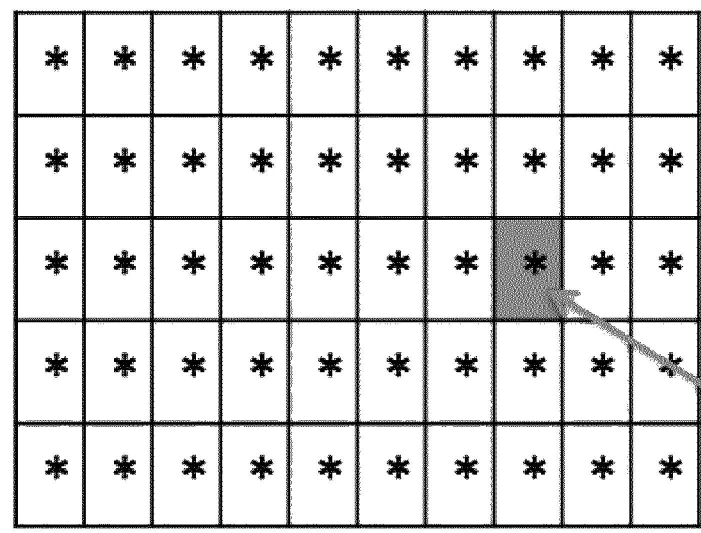
FIG. 2 schematically shows the structure of a coverage information table as input to the genomic data analyzer CNV detection module according a possible embodiment of the disclosure.
Figure 3A:
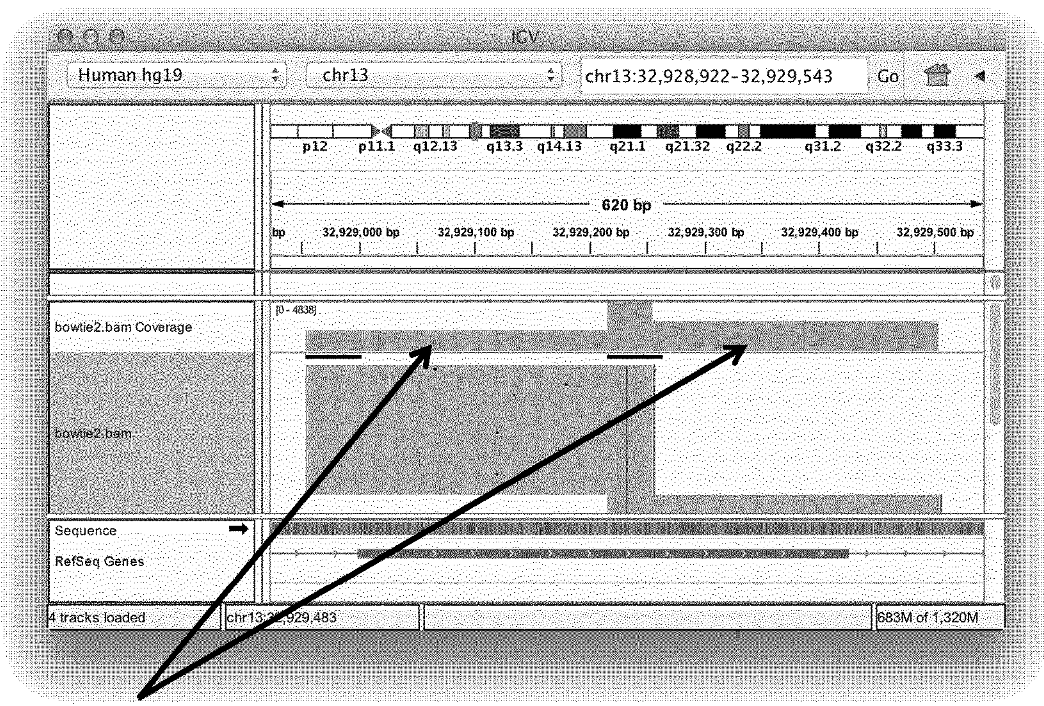
FIGS. 3*a* and 3*b* respectively illustrate exemplary (FIG. 3*a*) amplicon-based and (FIG. 3*b*) probe-based sample coverage information as retrieved and visualized with the IGV software from different state-of-the art targeted NGS platforms.
Figure 3B:
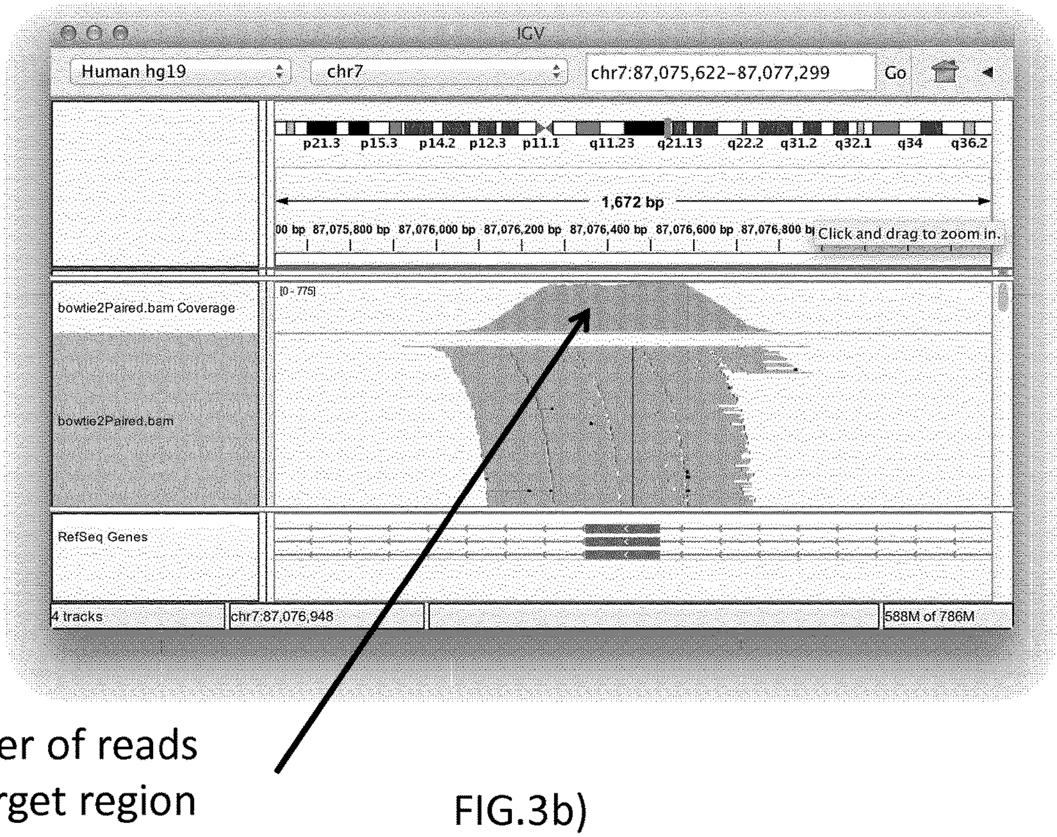

FIG. 2 schematically shows a coverage information table out of the coverage, where the rows represent amplicons (or suitably defined regions, in the case of a probe-based technology) and columns represent samples. The symbols '*' in the table represent the coverage information (coverage count) for each amplicon/region in each sample. This coverage count is defined as a suitable function of the numbers of forward reads, reverse reads, and read pairs (in case of pair-ended sequencing) corresponding to a given amplicon or region in a given sample. The definition of "correspondence" to an amplicon may be based on the match between the beginning and/or the end of the read to the beginning and/or end of the amplicon, and the "correspondence" to a region may be based on the overlap of the read with the region. However other suitable definitions may also be used in different embodiments. Additional filters based on the read parameters (for example, read length or mapping quality) may also be used. In one of the embodiments, the coverage is defined as the sum of the number of forward reads and the number of reverse reads, while in another embodiment the coverage is defined as the number of read pairs. In yet other embodiments other functions may be used (for example, using only forward-read or only backward-read counts, or the maximal of the two counts). Furthermore, depending on the properties of the target-enrichment assay, different functions may be used for different amplicons/regions. FIG. 3 illustrates possible choices of the coverage definition in amplicon-based and in probe-based designs, as viewed in IGV software using aligned reads. FIG. 3*a*) shows the amplicon coverage as the number of read pairs aligned to the corresponding region. FIG. 3*b*) shows the region coverage as the total number of reads (both forward and reverse) overlapping with a suitably chosen target region.

In the case where the CNV corresponds to a whole amplicon or region being duplicated, the NGS coverage corresponding to this region will be unusually high. Conversely, when the CNV corresponds to a whole amplicon or region being deleted, the NGS coverage corresponding to this region will be unusually low. It is therefore possible to detect CNVs by analyzing the coverage information distribution in the coverage information table across the amplicons/regions and across the samples. The coverage count $I_{a,s}$ may be approximately factorized into sample/plex-dependent and amplicon/region-dependent contributions:

$$I_{a,s}=R_{a,s}F_aP_{x,s}+\delta I_{a,s} \quad \text{(Eq. 1)}$$

where:

$I_{a,s}$ is the coverage count in the sample s for the amplicon (or region) a.

$F_a$ is the amplification factor specific for the amplicon (or region) a.

$P_{x,s}$ is the factor representing the amount of the DNA material processed for the sample s in the plex tube x (if applicable, for instance in the case of an amplicon-based technology with several plex tubes, where x specifies the plex for the amplicon a).

$\delta I_{a,s}$ is the coverage noise, which may be assumed to be small compared to the total coverage $I_{a,s}$. This overall coverage noise may result from various stages of the laboratory procedure (DNA extraction and targeted enrichment) and as well as from the sequencing technology itself. In a preferred simple model, the coverage noise may be modeled as $\delta I_{a,s}=\varepsilon^{(1)}_{a,s}I_{a,s}-\varepsilon^{(2)}_{a,s}\sqrt{I_{a,s}}$, where the first term represents the intensive part of the noise (proportional to the coverage count) and the second term represents the Poisson noise arising from random fluctuations of a finite number of sequencing reads (this contribution is proportional to the square root of the coverage count).

$R_{a,s}$ is the copy number value (the multiplicity of a given amplicon/region in a given sample) to be deduced by the proposed CNV detection method. In most cases (except for sex chromosomes and homologous regions), $R_{a,s}=2$ is the normal CNV value, and deviations from this normal value may indicate the presence of a CNV (for example, $R_{a,s}=1$ and $R_{a,s}=3$ may correspond to a heterozygous deletion and to a heterozygous duplication, respectively). Note that in germline samples, all cells are expected to carry the original individual genome DNA, so the copy number is an integer.

Since, even in the best laboratory conditions, different samples may have slightly different amplification factors $F_a$, CNV detection may be more reliable by comparing each sample to a selected group of "reference samples", chosen as the samples having the best correlations with the sample being tested, rather than comparing all samples together. In the case of several plexes, the reference samples may be different for different plexes.

The method assumes that the number of samples in one batch is sufficiently large (in a possible embodiment, the number of samples is at least eight, but other choices are also possible) and that the CNVs are sufficiently rare, so that for any amplicon/region the majority of samples have the regular copy number.

Figure 4:
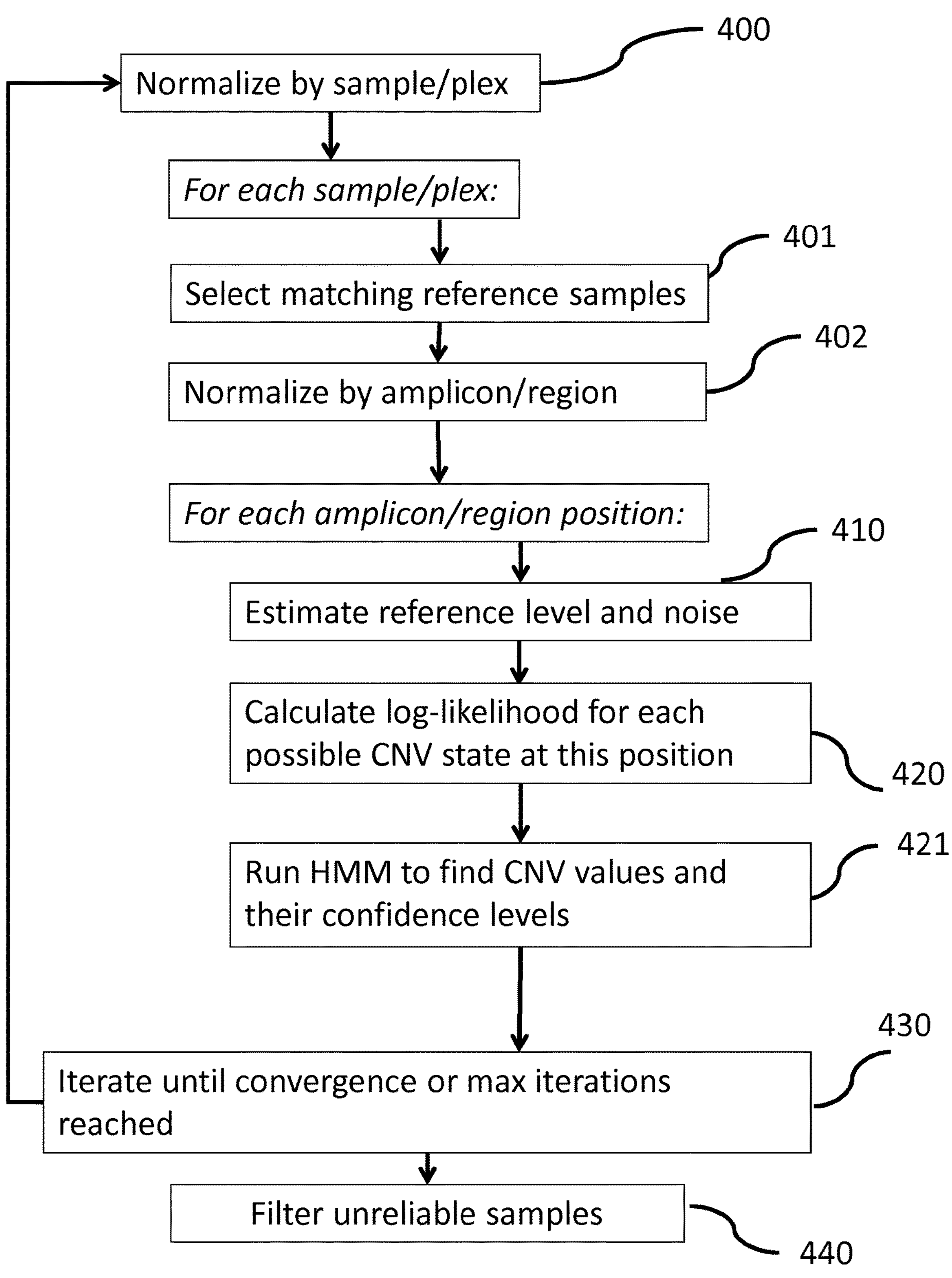
FIG. 4 shows a flowchart of a genomic data analyzer CNV detection module according a possible embodiment of the disclosure.

As represented on FIG. 4, the proposed method thus comprises the steps of:

Normalizing the coverage information by sample s (and plex x if applicable), taking into account an estimate of the copy number values detected in the previous iteration (if any) (400). In the first iteration, the regular (usual) copy number value may be used as an assumption, for instance 2.

For each sample s (referred to as "current sample" below):

Selecting a set of reference samples as the samples with normalized coverage having the closest coverage pattern to the normalized coverage of the current sample s (401);

Normalizing by amplicon/region a using the normalized coverage of the current sample and the normalized coverage from its selection of reference samples (402);

For each amplicon/region a in the current sample,

Estimating the reference level and noise (410);

For each amplicon/region a, estimating the likelihood for each possible copy-number value (CNV state) (420);

Based on the estimated likelihoods of copy-number values, identifying the actual copy-number values (CNVs) and their confidence levels (421).

Iterating from step (400), by taking into account the CNVs already detected in the previous iteration, until the detected CNVs stabilize or reach a cycle, or a maximum number of iterations is reached (430);

Filtering the samples by the residual noise and by CNVs found. Optionally, if necessary, repeat the whole procedure from the beginning with some samples excluded (440).

The individual steps will now be detailed as follows.

Sample- and Plex-Wise Normalization

Due to the specifics of the target enrichment experimental process, the raw coverage information out of the NGS workflow is not normalized. For instance there may be a different amount of DNA in each sample/plex, resulting in different coverage information values in the raw results along the sample/plex axis.

In a possible embodiment, in order to remove the sample/plex bias from the raw data set, the sample/plex-wise normalization step 400 may be taken as follows: the average over the sample/plex is determined as the mean of all the coverage counts $I_{a,s}$ normalized to a single copy, using the copy-number values $R_{a,s}$ calculated in the course of a previous iteration. The initial copy-number value for all amplicons of all samples/plexes may be set to the normal value (typically $R_{a,s}=2$, except in case of sex chromosomes and homologous regions). The coverage data may then be divided by the calculated mean, separately for each sample/plex, so that the resulting sample/plex-normalized coverage is of the order one:

$$I^{(norm)}_{a,s}=I_{a,s}/\text{mean}(I_{a',s}/R_{a',s}|\text{all amplicons/regions } a' \text{ in plex } x). \quad \text{(Eq. 2)}$$

In a possible embodiment, the regions with presumed homozygous deletions $R_{a,s}=0$ may be excluded from the mean calculation. In a possible embodiment, the mean is computed as the arithmetic mean. In another possible embodiment, the mean is computed as the geometric mean. Other embodiments are also possible. As will be apparent to those skilled in the art, different embodiments of the normalization method may also be used in different iterations of the CNV detection method.

Automated Selection of Reference Samples

The proposed method allows the automatic selection of reference samples from the normalized coverage information out of the target NGS experiment data, without requiring the user input to provide or manually select dedicated control samples, as will now be described in more detail.

In general, suitable reference samples may be automatically selected (step 401) by the CNV detection module 123 for each sample/plex as those having the closest coverage pattern to the current sample $s_0$. In a possible embodiment, the closest coverage pattern may be selected by calculating for every sample a distance from the current sample $s_0$, then sorting samples in order of increasing distance, and choosing a certain number of samples from the top of the list (having the smallest distances).

As will be apparent to those skilled in the art of statistics, there are many possible ways to define and calculate the distance between samples. In a possible embodiment, we first use the sample/plex normalized counts $I^{(norm)}_{a,s}$ to compute the sample/plex/amplicon/copy-number-normalized count as a vector $V_{a,s}$:

$$V_{a,s}=(I^{(norm)}_{a,s}/R_{a,s})/\text{median}(I^{(norm)}_{a,s'}/R_{a,s'}|\text{all samples } s'). \quad \text{(Eq. 3)}$$

In a possible embodiment, the regions with presumed homozygous deletions $R_{a,s}=0$ may be excluded from the median calculation.

In a possible embodiment, the distance between any sample s and the current sample $s_0$ may be defined as the Euclidean distance between the vectors $V_{a,s}$ and $V_{a,s0}$. In a possible embodiment, the correlation between the vectors $V_{a,s}$ and $V_{a,s0}$ may be computed.

In the case of amplicon-based technology with several plex tubes, the distances are preferably calculated separately for each plex x, possibly leading to different sets of reference samples for different plexes. For example, in the case of two plexes (e.g., for CFTR MASTR Multiplicom targeted enrichment kit), there may be two reference sets for each sample: one for each plex.

Other ways to define and calculate distance between samples are also possible. For example, one may use arithmetic or geometric mean in place of median or vise versa, or one may use other types of metric in place of Euclidean metric. The algorithm may also exclude certain regions or attribute different weights to different regions, depending on different criteria. In some embodiments, clustering algorithms may be used for assigning the distance. Other types of algorithms are also possible.

After calculating the distances between each sample and the current sample $s_0$, the reference samples may be chosen as a certain number of samples with the smallest distances. As will be understood by those skilled in the art, the number of reference samples should be chosen carefully. This number shall be sufficiently large for good statistical relevance; in particular, at each amplicon position, the set of reference samples should have the majority of normal copy numbers (no mutations). On the other hand, this number shall be sufficiently small so that only similar samples from the run are compared and outliers are filtered out.

In a possible embodiment, the number of reference samples $N_R$ may be selected as a function of the total number of samples N. In a possible embodiment, this function may be defined as:

$$N_R=[\alpha N+\beta\sqrt{N}+\gamma] \quad \text{(Eq. 4)}$$

with suitably chosen coefficients α, β, and γ, and [..] denoting the integer part. In a possible embodiment, parameters α, β, and γ may be chosen so that $N_R=[0.25*N]+2$, to select approximately 25% of samples as reference samples. Other choices of coefficients and, more generally, functions are also possible. In another embodiment, $N_R$ may depend not only on the total number of samples N, but also on other properties of the data, for example, on the level of fluctuations of the coverage count. Furthermore, in some embodiments, the number of reference samples may be different for different current samples $s_0$ (or for different plexes), for example, if the reference samples are selected as those at a distance below a certain cutoff distance from the current sample $s_0$. Other choices of algorithms for selecting reference samples based on the calculated distance are also possible.

While generally it may be beneficial to keep the number of reference samples $N_R$ smaller than the total number of samples N, in order to exclude noisy samples from references, in a possible embodiment, the number of reference samples $N_R$ may be equal to the total number of samples N.

In some embodiments, the choice of specific embodiments of calculating distances and/or of selecting reference samples may vary from iteration to iteration. For example, in a possible embodiment, in one of the iterations of the CNV detection (in one possible embodiment, specifically in the second iteration), the number of reference samples $N_R$ is taken to be equal to N: as a consequence, for this one iteration all the samples are used as reference samples. As will be apparent to those skilled in the art of bioinformatics, this flexible method may improve the detection performance in the case of frequent CNVs.

Amplicon-Wise Normalization

In addition to the plex/sample bias, there may also be coverage information divergences between different amplicons/regions, as the amplification efficiency tends to be region-dependent, thus also resulting into different coverage information values along the amplicons/region axis. Thus the plex-normalized data may be additionally normalized amplicon-wise in step 402 by the CNV detection module 123, for instance by dividing the coverage information by the median for each amplicon a, again using the coverage levels normalized to the assumed normal value of the copy number from the previous iteration (or the normal copy number in the first iteration). At this step, the normalization may be performed specifically within a reduced set of samples, including the reference samples as selected in step 401:

$$c_{a,s}=I^{(norm)}_{a,s}/\text{median}(I^{(norm)}_{a,s'}/R_{a,s'}|\text{reference samples } s') \quad \text{(Eq. 5)}$$

In one embodiment, the current sample $s_0$ may be included in the median calculation in addition to all reference samples. In another possible embodiment the current sample $s_0$ may be excluded from the median calculation. In a possible embodiment, the regions with presumed homozygous deletions $R_{a,s}=0$ may be excluded from the median calculation.

Estimating Reference Level and Noise for Each Amplicon or Region

At this stage of the proposed method, the following data have been computed for each sample s:

(1) the set of reference samples (for every plex x, if applicable);

(2) the sample/plex/amplicon normalized coverage levels $c_{a,s}$.

A further step 410 of estimating the reference coverage level and noise (uncertainty) may be further applied as follows.

First, the coverage levels $c_{a,s}$ may be converted into normalized coverage levels per copy by using the assumed copy-number value $R_{a,s}$ calculated in the previous iteration:

$$c^{(0)}_{a,s}=c_{a,s}/R_{a,s} \quad \text{(Eq. 6)}$$

In the very first iteration, the copy number may be assumed to be normal for all samples and for all amplicons/regions, for instance $R_{a,s}=2$.

Second, the reference normalized coverage level $C_a$ for each amplicon/region a may be estimated. In a possible embodiment, the normalized coverage level $C_a$ may be assumed equal to one. In another possible embodiment, the coverage level $C_a$ may be calculated as the mean of the normalized values) $c^{(0)}_{a,s}$ taken over the reference samples, with the outliers (values deviating from the mean more than a certain threshold, for instance three standard deviations) removed. Other choices of estimating the reference coverage levels are also possible, as will be understood by those skilled in the art of statistics.

Third, the noise level for each amplicon/region may be estimated. The noise level may be defined as the expected relative (divided by the mean) root-mean-square uncertainty of the coverage. In a possible embodiment, the noise level $\sigma_{a,s}$ may be estimated as $$\sigma_{a,s}=\max(\sigma_s, \sigma_a, 1/\sqrt{I_{a,s}}), \quad \text{Eq. (7)}$$

where:

$\sigma_s$ and $\sigma_a$ are the standard deviations of $c^{(0)}_{a,s}$ for the given sample and for the amplicon (within the set comprising the given sample and the reference samples).

$1/\sqrt{I_{a,s}}$ is the relative root-mean square deviation for the Poisson noise corresponding to the original coverage value $I_{a,s}$.

By using the standard deviations across the samples and across the amplicons, Eq. 7 takes into account the possibility of both noisy samples and noisy amplicons. For calculating $\sigma_a$, it may be beneficial to exclude outliers. In a possible embodiment, the data points outside the 3σ interval may be excluded. As will be apparent to those skilled in the art of statistics, other ways to estimate the noise level $\sigma_{a,s}$ may also be used, in place of Eq. 7.

In some embodiments, the step of estimating the reference normalized coverage level $C_a$ for each amplicon/region a may be modified in one of the first iterations (for example, in one possible embodiment, specifically in the first iteration), in order to detect CNVs that span a large fraction of all the amplicons/regions. In such a case, a simple normalization by sample may not enable to estimate a correct reference level. This problem may be solved using an additional algorithm that determines the reference level either on the basis of a special set of "control" amplicons/regions (that are assumed to be CNV free in their majority) or on the basis of the best match of the normalized levels to integers.

Calculating Likelihoods for Different Copy Numbers

At this step, the normalized coverage levels and the noise levels for each amplicon/region a and for each sample s may be further converted into log-likelihoods $L_a$ (defined as the minus logarithm of the likelihood of a particular coverage level, under the assumption of a given copy number and assuming a given noise level) (step 420). In a possible embodiment, the model of a Gaussian noise may be used for computing the log-likelihoods $L_a$:

$$L_a(r)=\min((c_{a,s}/(r\,C_a)-1)^2/(2\,\sigma_{a,s}^2), L_{max}), \quad \text{Eq. (8)}$$

where $c_{a,s}$, $C_a$, and $\sigma_{a,s}$ are respectively the coverage, the reference normalized coverage level, and the noise level for the current sample s and amplicon/region a. The log-likelihoods $L_a(r)$ may thus be calculated for all integer values of r ranging from 0 to a certain maximal value (in one embodiment, we have chosen the maximal value of r to equal 6, but other embodiments are also possible). In case r=0, Eq. 8 may be replaced by $L_a(0)=\min((c_{a,s}/C_a)^2/(2\sigma_0^2), L_{max})$, where $\sigma_0$ is the assumed noise level for a full deletion (in one embodiment, we chose $\sigma_0=0.01$, but other choices are also possible). The log-likelihood may be capped by a certain value $L_{max}$ in order to take into account that large fluctuations do not obey the normal distribution.

In some embodiments, $L_{max}$ may depend on the amplicon/region a. In other embodiments, other noise models may be used, in place of Eq. 8.

Finding CNVs and Their Confidence Levels

Using the log-likelihoods calculated in the previous step, the most likely CNV states may be found and their confidence levels may be calculated. In a possible embodiment, the Hidden-Markov-model (HMM) method may be used for this purpose (step 421). Examples of the use of HMM in CNV detection can be found for instance in S. Ivakhno et al., "*CNAseg—a novel framework for identification of copy number changes in cancer from second generation sequencing data*", *Bioinformatics* (2010) 26(24):3051-3058. Other embodiments are also possible, for instance a simple comparison of $L_a(r)$ with a suitably chosen threshold, similarly to the MLPA recommended procedure, as known to those skilled in the art.

In a possible embodiment, the HMM method may be realized by defining the HMM score as:

$$S_{HMM}(\{r_a\})=\Sigma_a(L_a(r_a)+p_{nb}(r_a)+p_{sw}(r_a,r_{a+1}), \quad \text{Eq. (9)}$$

where the HMM score $S_{HMM}(\{r_a\})$ is a function of the set of the assumed copy numbers $r_a$ for every amplicon/region in the current sample, $L_a(r_a)$ are the log-likelihoods calculated at the previous step, and $p_{nb}(r_a)$ and $p_{sw}(r_a r_{a+1})$ are additional penalties associated with the non-normal copy number and with a transition different copy numbers between neighboring amplicons/regions (denoted as a and a+1). The parameters $p_{nb}(r_a)$ and $p_{sw}(r_a,r_{a+1})$ may be chosen to provide a good performance and reflect the Bayesian prior expectations of having CNVs in the sample. In a possible embodiment, the functions $p_{nb}(r_a)$ and $p_{sw}(r_a,r_{a+1})$ may be chosen to be independent from the region/amplicon a, but in other embodiments they may themselves depend on the region/amplicon a. For example, in other possible embodiments, the functions $p_{nb}(r_a)$ and $p_{sw}(r_a,r_{a+1})$ may be functions of the length of the region, of the gaps between regions, of the possible overlaps between amplicons, or of the known collected statistics of CNVs in a given region. Other embodiments are also possible.

Once the HMM score is defined by Eq. 9, the forward-backward algorithm may be used, as known to those skilled in the art, to find the set of CNV states $\{r_a\}$ which minimize the HMM score and the set of "confidence" values. The confidence value at a position a may be defined as the minimal possible increase of the HMM score with the state $r_a$ differing from its optimal value. The statistical meaning of this confidence is the negative logarithm of the probability of error in determining $r_a$.

In practice, two versions of confidence may be introduced:

"numerical" confidence for determining the exact number of copies;

"variant" confidence for classifying the state as normal/insertion/deletion without specifying the exact value for the copy number (in case of insertions or deletions).

The "variant" confidence is thus always higher or equal than the "numerical" confidence.

All parameters may be further optimized for better performance and/or the HMM model may be adapted in various ways as will be apparent to one skilled in the art. Other models for HMM may also be applied. For instance, it may be worth using different penalties for insertions and deletions and introduce a dependence of the switching penalty on the difference between the CNV states $r_a$ and $r_{a+1}$, based on statistics for all sorts of possible CNVs.

Main Iteration

As apparent from the steps described above, the noise and reference-value calculations depend on the presumed copy-number values (the so-called "prior estimate of the copy-number values"), with the normal value, for instance 2, being the starting point. In order to determine the CNV states self-consistently, the algorithm may be iterated several times (step 430), using the result of the CNV detection at each iteration as the prior estimate of the copy-number values in the subsequent iteration. Practical experiments showed that, in case of high quality data, a few iterations are sufficient to efficiently detect the real CNV values. Sometimes (in case of noisy data), the iteration may enter a periodic cycle. In that case, the algorithm may be stopped as soon as a cycle pattern is detected.

Some of the targeted enrichment technologies may include so called "control amplicons/regions": amplicons or regions outside the regions of interest, typically broadly distributed across the genome. Such control amplicons may be used to normalize the coverage information. In one embodiment, only the coverage information from control amplicons is used in the sample/plex normalization (step 400) in the first iteration specifically. This may allow more robust detection of possible large CNVs (e.g., deletions of the whole gene) as in such a case, at the first iteration the copy-number value $R_{a,s}$ for the large CNV region will be set to the correct value and will preserve this value throughout subsequent iterations. Otherwise, the control amplicons may be used on the same footing as the test amplicons in the calculations of the noise and reference values, but they do not need to be included in the HMM part of the algorithm.

Final Filtering

After the last iteration, the proposed method provides the resulting values of the CNV levels as well as their confidence level. In a possible embodiment, a minimal threshold may be set for the confidence value, below which the results for individual amplicons may be assumed to be "unreliable" and may be filtered out from the results (step 440). In other embodiments, certain samples may also be excluded as "unreliable" based on the residual sample noise as or on the residual noise in one of the plexes or on the unrealistically large number of CNVs detected. The precise conditions of the labeling the sample as "unreliable" may depend on the details of the target-enrichment and sequencing technologies.

The CNV results for "unreliable" samples may be discarded from the final results in step 440. Finally, if too many samples (in one embodiment more than half of all the samples) are filtered out as "unreliable", the whole procedure may need to be repeated from the beginning, with the "unreliable" samples excluded. This option may provide better performance for runs where a large fraction of samples had technical problems at the initial target-enrichment or sequencing steps in the overall analysis workflow.

Optimization (Improvements)

In some embodiments, further improvements of the algorithm may be applied. One possible further embodiment may apply principal-component filtering, similar to M. Fromer et al., "*Discovery and statistical genotyping of copy-number variation from whole-exome sequencing depth*", *Am. J. Hum. Genet*. (2012) 91:597-607. A principal-component filter may be applied to the original dataset, for instance before the main CNV detection algorithm steps 400 to 430, or on the preliminary normalized dataset, for instance after normalization by sample/plex (step 401) or after normalization by amplicon/region (step 402). In one embodiment, the filter is trained once on a specially chosen training dataset and subsequently used without further updates. In other embodiments, the filter may include learning from new datasets.

In yet another embodiment, as represented on FIG. 1, the outcome from a parallel SNP/INDELs detection module 124 may also be used as an input to the CNV detection module 123 to further strengthen the CNV detection. In this case, the information on the coverage fraction for heterozygous SNPs may be used to bias the decision on the CNV values. For example, a 33% SNP fraction may be a strong argument in favor of a duplication (copy number equal 3). In a possible embodiment, this bias may be introduced at the HMM step 421 by adding a suitably chosen contribution to $p_{nb}(r_a)$ for a region, where one or several heterozygous SNPs are found.

In a further possible embodiment, the proposed CNV detection method may be adapted to the case of homologous (identical or nearly identical) regions or pseudogenes. In this case, the normal copy-number value may be different from 2 (e.g., in the case of one pair of homologous regions, the normal copy-number value equals 4). The CNV detection algorithm may be generalized to apply to this case by adjusting the normal copy number assumed value (e.g. from 2 to 4) and by using the total number of reads in all the regions homologous to the considered one in the main CNV algorithm steps 400 to 430. Additionally, the coverage differences between homologous regions may be used in a way similar to heterozygous SNPs in the former embodiment description to bias the parameters $p_{nb}(r_a)$.

Yet another situation where the normal copy number may differ from 2 is the case of sex chromosomes (X and Y chromosomes). In a possible embodiment, the normal copy number for regions in X and Y chromosomes is adjusted depending on the sex of the patient. In a further possible embodiment, the sex of the patient may be determined automatically by comparing the coverage information between X chromosome, Y chromosome, and autosomes, depending on their presence in the target amplification technology.

Experimental Results

The efficiency of the proposed method as depicted by the FIG. 4 flowchart to detect CNV variants has been compared to the MLPA method on an experiment comprising 474 samples in 11 batches originating from one laboratory, with the BRCA TrusSeq technology and MiSeq next generation sequencing pipeline. One known feature of the BRCA TruSeq assay is that it has many short amplicons, but the coverage noise is relatively high, and it does not have control amplicons. A deletion of a whole gene (BRCA1 or BRCA2) may nevertheless be detected from comparing the coverage levels between the genes in accordance with the proposed iterative method.

These samples contained 16 CNVs confirmed by MLPA. The same samples were analyzed independently using our CNV module. The results were then compared to the MLPA-confirmed variants. The detection sensitivity, measured as the percentage of the CNVs captured by the algorithm in comparison to the MLPA method, was measured at 100%, i.e. all 16 CNVs were successfully detected. Moreover, the percentage of samples with rejections or false positives recommended for re-testing for CNVs by either the same or an alternative method (the lower the better) was measured at 4.2% while a maximum value of 10% may be acceptable in the case of the best laboratory practice. The proposed genomic data analysis method therefore enables to reach similar CNV detection sensitivity and accuracy as the state of the art MLPA method, while enabling the use of a single target NGS experiment pipeline, which brings significant practical advantages in research or clinical practice.

Other Embodiments and Applications

Although the detailed description above contains many specific details, these should not be construed as limiting the scope of the embodiments but as merely providing illustrations of some of several embodiments.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methods are sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed:

1. A method for detecting copy-number values (CNV), wherein the detection of CNVs is integrated into a single, targeted high-throughput sequencing experiment, the method comprising the steps of:

(A) enriching a pool of DNA samples with a target enrichment technology, each enriched DNA sample being associated with a library of pooled fragments from a set of amplicons/regions;

(B) sequencing each amplicon/region with a high-throughput sequencer to generate raw sequencing data; and (C) analyzing the raw sequencing data with a genomic data analyzer to determine the CNVs for each sample and each amplicon/region, comprising:

(i) cleaning the sequencing data to remove low-quality bases and adapter sequences, and aligning the cleaned reads to a reference genome;

(ii) generating from the aligned cleaned reads, with a data processing unit, a coverage count for each sample and for each amplicon/region; and (iii) repeating, with a data processing unit, over a plurality of iterations, the following steps to estimate the copy-number values for each sample and for each amplicon/region:

(a) normalizing, with the data processing unit, the coverage count associated with each sample based on a prior estimate of the copy number values for each sample, wherein, if a first iteration of a plurality of iterations, the prior estimate of the copy number values is an initial estimate of the copy-number values, and wherein, if not the first iteration of a plurality of iterations, the prior estimate of the copy number values is the copy-number values calculated in the course of a previous iteration;

(b) selecting, automatically, with the data processing unit, for each sample, a set of reference samples as the samples with the closest normalized coverage count to the normalized coverage count of said sample, the number of reference samples in each subset of reference samples being a function of the total number of samples, wherein the selecting of the reference samples does not require the use of specifically chosen, dedicated control samples, and wherein the closest coverage pattern is selected by calculating for each sample a distance from a current sample and sorting said samples in order of increasing distance, and choosing the set of reference samples from the top of said order having the smallest distances;

(c) normalizing the coverage count associated with each amplicon/region based on the normalized coverage count of the current sample and the normalized coverage count of said set of reference samples, and (d) for each sample, estimating, using a Hidden Markov Model (HMM), the copy-number values in said sample as a function of at least the coverage counts in said sample and of at least the coverage counts in the selected set of reference samples for said sample and utilizing the estimate of the copy-number values calculated over previous iterations; and (e) stopping the iteration and outputting the inferred copy-number values if the estimates of the copy-number values converge over iterations, if the estimates of the copy-number values reaches a cycle over multiple iterations, or if the number of iterations reaches a pre-defined limit.

2. The method of claim 1, wherein the number of reference samples NR in each set of reference samples is given by NR=[0.25*N]+2, where N is the total number of samples.

3. The method of claim 1, wherein the estimate of the copy-number values is calculated using information on the single-nucleotide polymorphisms (SNP) fractions and coverage, and wherein a percentage of SNP fractions is indicative of a duplication.

4. The method of claim 1, further comprising: applying a principal-component filter to the coverage count generated for each sample and for each amplicon/region.

5. The method of claim 1, wherein normalizing the coverage count associated with each sample in one iteration differs from normalizing the coverage count associated with each sample in subsequent iterations.

6. The method of claim 1, wherein selecting the reference samples in one iteration differs from selecting the reference samples in subsequent iterations.

7. The method of claim 5, wherein the number of reference samples in one iteration differs from the number of reference samples in subsequent iterations.

8. The method of claim 7, wherein in one iteration the number of reference samples in a set equals the total number of samples N, and wherein in subsequent iterations the number of reference samples in a set is different from the total number of samples N.

9. The method of claim 1, wherein the step of estimating, using a Hidden Markov Model (HMM), the copy number values in the said samples as a function of at least the coverage counts in the selected set of reference samples for said sample and utilizing the estimate of the copy-number values calculated over the plurality of iterations, further comprises the step of:

estimating, via the HMM, a likelihood for each of the copy-number values and a confidence level for each amplicon/region.

10. The method of claim 9, wherein the step of estimating, via the HMM, a likelihood for each of the copy-number values and a confidence level for each amplicon/region, further comprises the steps of:

determining the likelihood for each copy-number value as a log-likelihood, the log-likelihood being defined as $$L_a(r)=\min((c_{a,s}/(r\ C_a)-1)^2/(2\ \delta_{a,s}^2),\ L_{max})$$

wherein $C_{a,s}$, $C_a$, $\delta_{a,s}$ are, respectively, a coverage level, a reference normalized coverage level, and a noise level for the current sample s and amplicon/region a, determining an HMM score defined as $$S_{HMM}(\{r_a\})=\Sigma_a(L_a(r_a)+P_{nb}(r_a)+P_{sw}(r_a,r_{a+1})$$

wherein the HMM score, $S_{HMM}(\{r_a\})$, is a function of a set of assumed copy numbers $r_a$ for every amplicon/region in the current sample, $L_a(r_a)$ are the log-likelihoods calculated at the previous step, and $p_{nb}(r_a)$ and $p_{sw}(r_a r_{a+1})$ are additional penalties associated with a non- normal copy number and with a transition between different copy numbers among neighboring amplicons/regions, denoted as $\alpha$ and $\alpha+1$, and finding a set of CNV states $\{r_a\}$, via a forward-backward algorithm, which minimize the HMM score and the set of confidence values, each confidence value at a position a defined as the minimal possible increase of the HMM score with the state $r_a$ differing from its optimal value.

11. The method of claim 10, further comprising the step of excluding each of the copy-number values with the confidence level for each amplicon/region below a threshold.

12. The method of claim 1, further comprising the step of excluding each of the copy-number values with a confidence level for each amplicon/region below a threshold.

* * * * *